United States Patent [19]

Fisher et al.

[11] 4,203,976

[45] May 20, 1980

[54] SUGAR DERIVATIVES OF C-076 COMPOUNDS

[75] Inventors: Michael H. Fisher, Bridgewater; Richard L. Tolman, Berkeley Heights, both of N.J.

[73] Assignee: Merck & Co., Inc., Rahway, N.J.

[21] Appl. No.: 930,466

[22] Filed: Aug. 2, 1978

[51] Int. Cl.² .................. A61K 31/35; C07H 17/08
[52] U.S. Cl. ..................... 424/180; 260/343.41; 536/17 A; 424/279
[58] Field of Search ............... 536/9, 17; 424/180

[56] References Cited

U.S. PATENT DOCUMENTS

| | | | |
|---|---|---|---|
| 3,950,360 | 4/1976 | Aoki et al. | 536/17 |
| 4,020,270 | 4/1977 | Arcamone et al. | 536/17 A |
| 4,025,623 | 5/1977 | Arcamone et al. | 536/17 A |
| 4,039,663 | 8/1977 | Arcamone et al. | 536/17 A |

FOREIGN PATENT DOCUMENTS 2717040 10/1977 Fed. Rep. of Germany ............ 536/17

*Primary Examiner*—Johnnie R. Brown
*Attorney, Agent, or Firm*—David L. Rose; Harry E. Westlake

[57] ABSTRACT

Derivatives of C-076, a series of macrolides, are described in which the substituents are sugar or saccharide groups. The sugar groups are substituted on any of the available hydroxy groups of the C-076 molecule. The compounds thus produced have profound anthelmintic, insecticidal, ectoparasiticidal and acaracidal activity and compositions for such uses are also disclosed.

18 Claims, No Drawings

SUGAR DERIVATIVES OF C-076 COMPOUNDS

BACKGROUND OF THE INVENTION

The term C-076 is used to describe a series of compounds isolated from the fermentation broth of a C-076 producing strain of Streptomyces avermitilis. The morphological characteristics of the culture are completely described in copending U.S. Pat. application Ser. No. 772,601 filed Feb. 28, 1977 and now abandoned. The C-076 compounds are a series of structurally related macrolides, with one or more hydroxy substituents which are capable of being substituted with a sugar molecule. With respect to the C-076 compounds which have more than one hydroxy group, procedures have been developed for the selective glycosylation at the various position.

In addition, derivatives of the C-076 compounds have been prepared and such derivatives have been glycosylated by the presence of this invention. The glycosylated compounds thus prepared have profound; anthelmintic, insecticidal, ectoparasiticidal and acaricidal activity.

SUMMARY OF THE INVENTION

This invention is concerned with the glycosylation products of the C-076 compounds and derivatives of C-076 compounds. The glycosylated products are very active antiparasitic agents. Thus, it is an object of this invention to describe such glycosylated products. It is a further object of this invention to describe the processes employed in the preparation of such glycosylated products. A still further object of this invention is to describe the use of such compounds as antiparasitic agents. Additional objects will become apparent from a reading of the following description.

DESCRIPTION OF THE INVENTION

The C-076 series of compounds have the following structure:

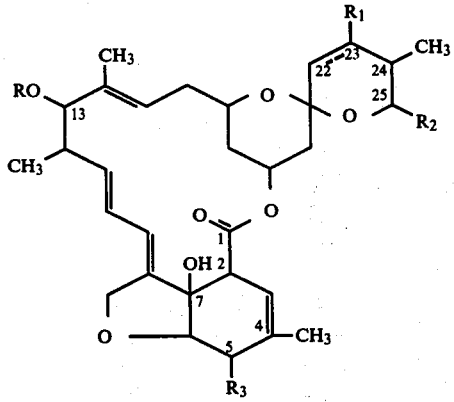

wherein R is the α-L-oleandrosyl-α-L-oleandrosyl group of the structure:

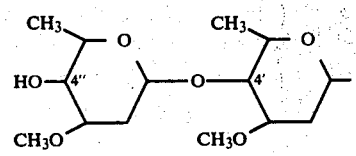

and wherein the broken line between $C_{22}$ and $C_{23}$ indicates a single or a double bond; $R_1$ is hydroxy and is present only when said broken line indicates a single bond;

$R_2$ is n-propyl or sec-butyl; and
$R_3$ is methoxy or hydroxy.

There are eight different C-076 compounds and they are given the designation A1a, A1b, A2a, A2b, B1a, B1b, B2a, B2b based upon the structure of the individual compounds.

In the foregoing structural formula, the individual C-076 compounds are as set forth below.

|  | $R_1$ | $R_2$ | $R_3$ |
|---|---|---|---|
| A1a | Double bond | sec-butyl | —OCH$_3$ |
| A1b | Double bond | iso-propyl | —OCH$_3$ |
| A2a | —OH | sec-butyl | —OCH$_3$ |
| A2b | —OH | iso-propyl | —OCH$_3$ |
| B1a | Double bond | sec-butyl | —OH |
| B1b | Double bond | iso-propyl | —OH |
| B2a | —OH | sec-butyl | —OH |
| B2b | —OH | iso-propyl | —OH |

As is readily seen, all of the C-076 compounds have hydroxy group at the 7-position and the 4″-position of the carbohydrate side chain. Thus all of the compounds have at least two hydroxy groups capable of being glycosylated. In addition, the A2 and B1 series of compounds have a third hydroxy group and the B2 series of compounds has a fourth hydroxy group which may be glycosylated.

The carbohydrate side chain may also be hydrolyzed to remove one or both of the α-L-oleandrose groups. In this case there would remain a hydroxy group at the 4′ or 13-position with the removal of a single α-L-oleandrose (monosaccharide) or both α-L-oleandrose (agylcone) respectively. These hydroxy groups may readily be glycosylated.

The monosaccharide and aglycone derivatives are prepared by the treatment of the parent C-076 compound with acid. The outer α-L-oleandrose group is more easily removed than the α-L-oleandrose group directly bonded to the C-076 substrate thus facilitating the separate preparation of the monosaccharide and aglycone without contamination with the other reaction product.

The process employed for the removal of the C-076 carbohydrate group or groups is to put the C-076 starting material in solution in a mixture of from 0.01 to 10% acid in a non-nucleophilic water miscible solvent such as dioxane, tetrahydrofuran, dimethoxyethane, dimethylformamide, bis-2-methoxyethyl ether and the like, and from 0.1 to 20% water. The mixture is stirred for from 6 to 24 hours at room temperature to complete the reaction. Acids such as sulfuric, hydrochloric, hydrobromic, phosphoric, trifluoroacetic and trifluorosulfonic are acceptable. Sulfuric acid is preferred.

When lower acid concentrations such as from 0.01 to 0.1% are employed, the monosaccharide is predominantly prepared. When higher concentrations of acid are employed, such as in the range of 1 to 10%, the aglycone is predominantly prepared. Intermediate concentrations of acid will tend to prepare mixtures of monosaccharide and aglycone which are generally separable using chromatographic techniques.

The monosaccharide may also be prepared by stirring the C-076 precursor for from 6 to 24 hours at room temperature in 1% sulfuric acid in isopropanol. In addition the aglycone can be prepared by stirring the C-076 precursor for from 6 to 24 hours at room temperature in 1% sulfuric acid in methanol. The other acids listed above may also be employed in this process. This process is preferred for us with the 2- series of C-076 compounds since some addition may be observed to the 22,23 double bond of the series of C-076 compounds with a 22,23 unsaturation. The desired monosaccharide or aglycone are isolated and purified using techniques known to those skilled in the art.

The glycosyl compounds of this invention are best realized in the following structural formula:

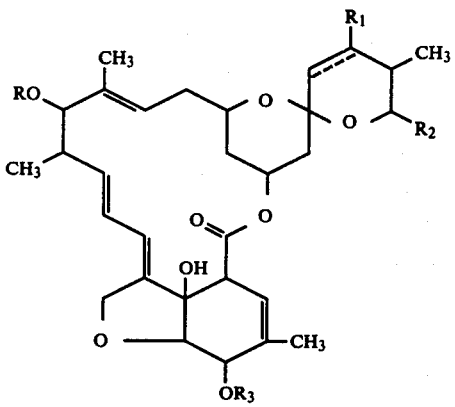

wherein the broken line indicates a single or a double bond;

$R_1$ is hydroxy, loweralkanoyloxy or glycosyloxy and is present only when the broken line indicates a single bond;

$R_2$ is iso-propyl or sec-butyl;

$R_3$ is hydrogen, methyl, loweralkanoyl or glycosyl; and

R is hydrogen, loweralkanoyl, glycosyl,

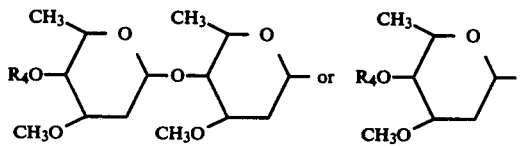

wherein $R_4$ is hydrogen, loweralkanoyl or glycosyl;

provided that at least one of R, $R_1$, $R_3$ or $R_4$ must contain a glycosyl group, however if only R contains a glycosyl group, such glycosyl group should be other than α-L-oleandrosyl or α-L-oleandrosyl-α-L-oleandrosyl. Said glycosyl groups are polyhydroxy 5 or 6 membered cyclic acetals which are optionally substituted with loweralkyl and in which the hydroxy groups may be optionally substituted with loweralkyl or loweralkanoyl and the monounsaturated derivatives thereof.

In the instant application the term "loweralkanoyl" is intended to include those alkanoyl groups of from 2 to 10 carbon atoms such as acetyl, propionyl, butyryl, pentanoyl, hexanoyl, pivaloyl, octanoyl, decanoyl, and the like.

The nature of the sugar moiety in the above glycosyl groups is not critical and any sugar may be substituted onto the C-076 substrate using the procedures described below. The preferred sugar moieties are glucopyranosyl, galactopyranosyl, mannopyranosyl, maltosyl, arabinopyranosyl, lyxopyranosyl, xylopyranosyl, ribopyranosyl, oleandrosyl, rhamnopyranosyl, fucopyranosyl, lactosyl, ribofuranosyl, mannofuranosyl, glucofuranosyl, arabinofuranosyl, mycarosyl, cladinosyl, desosaminosyl, daunosaminosyl, mycaminosyl, cymarosyl, olivosyl and the like.

The foregoing sugars are available generally in the D or L configuration. The instant invention includes both the possible configurations for attachment to the C-076 substrate.

The above carbohydrate or sugar groups may be substituted on the C-076 compounds as mono, di or trisaccharides wherein one of the above sugar groups is further substituted with another of the same or different sugar. In addition, where there is more than one hydroxy group available for substitution, the sugar groups may be present on only one or on more than one of such hydroxy groups, and the substitution may be with identical or different sugar moieties.

The preferred sugar substituents are mono- or disaccharide substitution with glucopyranosyl, rhamnopyranosyl, oleandrosyl or olivosyl groups. The most preferred groups are glucopyranosyl and oleandrosyl.

The processes for the substitution of the carbohydrate groups onto the hydroxy groups of the substrate molecule the Koenigs-Knorr process, the silver triflate process the orthoester process, or the glycol addition process.

The carbohydrate starting materials employed for the Koenigs-Knorr, the Helferich modification thereof and the silver triflate processes are protected by acylating all of the free hydroxy groups. The preferred protecting group is the acetyl group, however, other groups such as the benzoate may be employed. The processes for the blocking of the hydroxy groups are well known to those skilled in the art. The acetyl blocking groups are also easily removed at the completion of the reaction by catalytic hydrolysis, preferably base-catalyzed hydrolysis such as with an alcoholic ammonia solution The Koenigs-Knorr and silver triflate processes use as starting materials the acetohalosugars preferably the acetobromo sugars such as the appropriate acetobromohexoses and acetobromopentoses of the sugar groups listed above. The bromine atom is substituted on a carbon atom adjacent to an acetyl group and the sugar moiety become bonded to the substrate at the carbon atom to which the halogen was attached.

In the Koenigs-Knorr reaction the C-076 compound is dissolved under anhydrous conditions in an aprotic solvent. Ether is the preferred solvent, however, methylene chloride, acetonitrile, nitromethane, dimethoxyethane and the like may also be employed. To the substrate solution is added the acetohalosugar and silver oxide. A single molar equivalent of the sugar is required for the reaction, however, an additional 10 to 15 moles occasionally aids the reactions. Additional molar excesses beyond 15 may be employed in difficult reactions, however, such very large excesses tend to make the isolation of the product more difficult. It has been found preferable to employ freshly prepared silver oxide for the reaction, since the material tends to lose some of its catalytic efficiency upon standing for prolonged periods. The silver oxide is prepared from silver nitrate using known procedures. The reaction may be carried out at from 10°–15° C., however, reaction at room temperature is preferred. The reaction generally requires from 2 to 10 days for completion. Reaction progress is monitored by taking aliquots from the reaction mixture and examing them with thin layer chromatographic techniques. Possible side reactions are avoided by carrying out the reaction in the dark, and this method is preferred. The product is isolated using techniques known to those skilled in the art.

In one modification of the Koenigs-Knorr reaction, known as the Helferich modification thereof, a mercuric halide, such as mercuric chloride or bromide, alone or in combination with mercuric oxide or mercuric cyanide is substituted for the silvoxide. The above described reaction conditions be employed except that nitromethane and benare the preferred solvents and reflux temperature is the preferred reaction temperature.

The silver triflate reaction uses the reagent silver triflate (silver trifluoromethyl sulfonate) and the acetohalosugar in the same solvents listed above, with ether being preferred. The silver triflate is best if highly purified and freshly prepared just prior to its use. Methods for the preparation of silver triflate are well known to those skilled in the art. All of the reactants are combined in the solvent and the reaction conducted at from 10° to 50° C. for from 2 to 48 hours. Generally, however, the reaction is complete in about 24 hours at room temperature. The progress of the reaction may be followed by thin layer chromatography techniques. Again the reaction is preferably carried out in the dark, and with absolutely dry reactants and equipment.

A single mole of the sugar is required, however, a single molar excess is often used to aid in the course of the reaction.

During the course of the reaction a mole of triflic acid (trifluoromethanesulfonic acid) is liberated. This is a very strong acid and a molar equivalent of a base is required to neutralize the acid. Preferred bases are non-nucleophilic bases such as tertiary amines, preferably triethylamine, diisopropylethylamine, diazabicycloundecane, diazabicyclononane and the like. Since triflic acid is such a stron acid, if the base used is not a strong enough base to neutralize all of the acid, the residual acid will adversely affect the course of the reaction and of the isolation of the product. The product is isolated using techniques known to those skilled in the art.

The orthoester process prepares sugar derivatives of the C-076 compounds from orthoesters of a lower alkanol and of the above sugars at the hydroxy function of said C-076 compounds. The ortho-esters are prepared from the acetohalosugars using a loweralkanol and procedures which are well known to those skilled in the art. The reaction is carried out in an aprotic solvent such as dichloroethane, nitromethane, methylene chloride, dimethoxy ether, acetonitrile, tetrahydrofuran and the like. Dichloroethane, nitromethane, dimethoxy ethane and tetrahydrofuran are preferred. The reaction is preferably carried out at the reflux temperature of the reaction mixture and is generally complete in from about 4 to 24 hours. Catalytic amounts of mercuric bromide or mercuric chloride are added to aid in the reaction. During the course of the reaction one mole of the alcohol used to make the orthoester is liberated. Thus, the preferred method is to azeotropically distill off the solvent to remove the alcohol and to force the reaction to completion. To prevent any volume reduction, fresh solvent is added as the distillation proceeds to maintain a constant volume. To isolate the product, the solvent is generally removed and the residue washed with a reagent to remove the mercury salts, such as aqueous potassium iodide. The product is then isolated using known techniques.

Another glycosylation procedure has been developed which employs glycal starting materials. Glycals are 1,2-unsaturated cyclic sugars where the ring is a 6 membered ring. The reaction provides for the substitution of the glycosyl moiety onto the C-076 substrate in two ways, depending on the substitution at the 3-position of the sugar ring. Where the 3-position is substituted with a leaving group, such as a loweralkanoyloxy, such as acetate, substituted phenylsulfonate, such as a tosylate, the leaving group is eliminated and the double bond shifts to the 2,3-position and the 3-position in the resultant product is unsubstituted.

If the 3-position group is not a leaving group, such as loweralkoxy, preferably methoxy, the group is not eliminated and the 3-position remains intact. The reaction produces an addition across the double bond, and the resultant saturated product is attached to the C-076 substrate at the 1-position.

The reaction is carried out in an aprotic, non-polar solvent or, since the glycal starting materials are often liquids at room temperature, the reaction may be carried out neat. Preferred solvents are halogenated hydrocarbons such as methylene chloride, chloroform and the like, acetonitrile, benzene, toluene, ether and the like. In addition, the reaction may contain a catalytic amount of a Lewis Acid such as boron trifluoride, tin chloride ($SnCl_2$) titanium, tetrachloride, zinc chloride ($ZnCl_2$) and the like or other acid catalyst ($\beta$-toluenesulfonic acid, pyridinium $\beta$-toluenesulfonate). The reaction is carried out at from room temperature to the reflux temperature of the reaction mixture, however usually maximum temperatures of 75° C. are adequate. The reaction is complete in from ½ to 24 hours and the product is isolated using known techniques.

With respect to the foregoing glycosylation reactions, it is noted that the B-series of compounds are preferably glycosylated using the Koenigs-Knorr or glycal addition reaction. This is because the B-compounds are somewhat sensitive to the mercury compounds used in the Helferich modification.

Because of the different reactivities of the various hydroxy groups, and with the use of certain protecting techniques, all possible combinations of glycosylated C-076 compounds can be prepared. The hydroxy groups at the 5 and 23 positions are much more reactive to glycosylation than the 4″, 4′ or 13 positions. Thus, where the 5 or 23 glycosylated products are desired, no protection is necessary for the 4″, 4′ or 13 positions.

The C-076 Al compounds have only the 4″, 4′ or 13 positions available for glycosylation, thus no reaction is possible at the 5 or 23 positions.

The C-076 A2 compounds have only the 23-hydroxy group available for glycosylation, in addition to the 4″, 4′ or 13 positions. Thus, the 23 glycosyl compound can be prepared with no protection reactions necessary. The 4″, 4′ or 13 positions can be glycosylated by protecting the 23-position following the procedure described below.

The C-076 B1 compounds have only the 5-position available in addition to the 4″, 4′ or 13 positions. If the 5-glycosyl compounds are desired, the reaction is carried out without the protection of the 4″, 4′ or 13 positions. If the 4″, 4′ or 13 glycosyl compounds are desired, protection of the 5-position following the procedure described below is required.

The C-076 B2 compounds have both the 5 and 23 positions available for glycosylation in addition to the 4″, 4′ or 13 positions. The reactivity of the 5- and 23- position hydroxy groups are about equal. If glycosylation at the 5 and 23 positions is desired, the reaction is carried out as above described. If glycosylation at the 4″, 4′ or 13 positions is desired, protection of both of the 5 and 23 hydroxy groups is necessary. If glycosylation of only one of the 5- or 23-positions is desired, the reaction is carried out as above described using minimal times and temperatures within the ranges given, thus resulting in a mixture of 5- and 23-glycosyl compounds. Such a mixture is readily separated, usually with chromatographic techniques such as column, high pressure, liquid chromatography and thin layer or preparative layer chromatography. The technique of thin layer chromatography is usually employed to follow the course of the reaction in order to maximize the formation of the individual 5- and 23-substituted compounds and to avoid the formation of the 5,23-disubstituted compounds.

The protection of the 5 and 23 positions is carried out in two ways; one applicable to the 5 and 23 positions, and the other applicable to the 5-position only.

The 5 and/or the 23 positions may be readily protected by acylating, preferably acetylating. The C-076 compound to be protected is dissolved in an aprotic, non polar solvent, such as one of such solvents described above preferably ether and an acyl halide, preferably acetyl chloride, is added dropwise substantially at room temperature but up to a 10°-40° C. range. The reaction mixture is stirred for from 2 to 6 hours. A catalytic amount of silver oxide ($Ag_2O$) is added to the reaction. The acylated compound is isolated using known techniques.

The acyl protecting group may be removed by base catalyzed hydrolysis, such as with an alkali metal alkoxide, preferably sodium methoxide, in the corresponding alcohol, preferably methanol.

In addition, the 5-position alcohol may be oxidized to the ketone using manganese dioxide ($MnO_2$) in ether. The reaction is completed in about 10 to 30 hours at about room temperature.

The ketone is then readily converted back to the hydroxy group using borohydride reduction, preferably sodium borohydride. The reaction is complete in about 5 minutes to 1 hour with stirring substantially at room temperature.

This oxidation-reduction reaction sequence is seen to aid in the preparation of C-076 B2 compounds with only one of the 5- or 23-positions glycosylated. By protecting the 5-position with the preparation of the 5-ketone the 23-glycosyl compound may readily be prepared. Or the 23-acyl-5-ketone compound can be prepared, the 5-position reduced to the hydroxy group, and the 5-glycosyl compound prepared.

It is noted that the acyl derivatives are included within the ambit of this invention, thus, if desired the acyl protecting groups need not be removed at the end of a reaction sequence. In addition, once the glycosyl compounds are prepared, at the desired position or positions, any remaining hydroxy groups may be acylated. The foregoing procedure may be employed to acylate the 5- and 23-positions. Where glycosylation has occurred or is planned for the 5- and/or 23-positions the 4″, 4′ or 13 position may be acylated by dissolving the compound in a suitable solvent, preferably pyridine, and adding the acylating reagent, preferably a loweralkanoyl halide, such as acetyl chloride, dropwise. The reaction is maintained at from 0° C. to room temperature for from 4 to 24 hours. The product is isolated using known techniques.

The novel glycosylated compounds of this invention have significant parasiticidal activity as anthelmintics, insecticides, ectoparasiticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostronglylus, Ostertagia, Nematodiurs, Cooperia, Ascaris, Bunostomum, Oesophagostomum, Chabertia Trichuris, Stronglylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The glycosylated C-076 compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp. and the housefly *Musca domestica.*

The compounds are also useful against insect pests of stored grains such as Tribolium sp., Tenebrio sp. and of agricultural plants such as spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the C-076 compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and Content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparations using solketal, glycerol-formal and aqueous parenteral formulations are also used. The active acylated C-076 compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting and sucking insects in domesticated animals and poultry. They are also effective in treatment of parasitic diseases that occur in other aimals including humans. The optimum amount to be employed for best results will, of course, depend upon the particular compound employed, the species of animal to be treated and the type and severity of parasitic infection or infestation. Generally, good results are obtained with our novel compounds by the oral administration of from about 0.001 to 10 mg. per kg. of animal body weight, such total dose being given at one time or in divided doses over a relatively short period of time such as 1–5 days. With the preferred compounds of the invention, excellent control of such parasites is obtained in animals by administering from about 0.025 to 0.5 mg. per kg. of body weight in a single dose. Repeat treatments are given as required to combat reinfections and are dependent upon the species of parasite and the husbandry techniques being employed. The techniques for administering these materials to animals are known to those skilled in the veterinary field. The compounds may also be administered in combination with other antiparasitic compounds or compounds with other biological activities to provide for a single treatment with a broadened spectrum of activity.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active glycosylated C-076 compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular glycosylated C-076 compound employed, the compounds of this invention are usually fed at concentrations of between 0.00001 to 0.002% in the feed in order to achieve the desired antiparasitic result.

In using the compounds of this invention, the individual glycosylated C-076 components may be prepared and used in that form. Alternatively, mixtures of two or more of the individual glycosylated C-076 compounds may be used.

In the isolation of the C-076 compounds, which serve as starting materials for the instant processes, from the fermentation broth, the various C-076 compounds will be found to have been prepared in unequal amounts. In particular an "a" series compound will be prepared in a higher proportion than the corresponding "b" series compound. The weight ratio of "a" series to the corresponding "b" series is about 85:15 to 99:1. The differences between the "a" series and "b" series is constant throughout the C-076 compounds and consists of a butyl group and a propyl group respectively at the 25 position. This difference, of course, does not interfere with any of the instant reactions. In particular, it may not be necessary to separate the "b" components from the related "a" component. Separation of these closely related compounds is generally not practiced since the "b" compound is present only in a very small percent by weight, and the structural difference has negligible effects on the reaction processes and biological activities.

The C-076 compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that the invention might be more fully understood; they are not to be construed as limitations of the invention.

The C-076 glycosyl derivatives prepared in the following examples are generally isolated as amorphous solids and not as crystalline solids. They are thus characterized analytically using techniques such as mass spectrometry, nuclear magnetic resonances and the like. Being amorphous, the compounds are not characterized by sharp melting points, however the chromatographic and analytical methods employed indicate that the compounds are pure.

EXAMPLE 1

4'-O-(2,3,4,6-tetra-O-acetyl-$\beta$-D-glucopyranosyl) C-076 $A_{2a}$ monosaccharide A 3-necked flask is charged with C-076 $A_{2a}$ monosaccharide (50 mg.), 3,4,6-tri-O-acetyl-1,2-O-(ethylorthoacetyl)-X-D-glucopyranose (50 mg.), mercuric bromide (2 mg.) and dichloroethane (20 ml.). The flask is fitted into a dropping funnel containing fresh, dry solvent and a Dean-Stark Trap. The mixture is heated at reflux under nitrogen and as the solvent is slowly distilled from the reaction mixture, it is replaced with fresh solvent from the dropping funnel. After 24 hours of refluxing, thin layer chromatographic monitoring indicates no further reaction progress and the mixture is cooled, filtered (discarding all solids), and the filtrate evaporated to dryness in vacuo. Chromatographic resolution of the mixture on preparative layer chromatography [silica gel, multiple development with benzene/2-propanol (19:1)] affords a large amount of starting material, some minor side products and 16 mg. of 4'-O-(2,3,4,6-tetra-O-acetyl-$\beta$-D-glucopyranosyl) C-076 $A_{2a}$ monosaccharide, which is lyophlized from benzene. The structure is consistent with mass spectral and 300 MHz nuclear magnetic resonance analysis.

EXAMPLE 2

4''-O-(2,3,4,6-tetra-O-acetyl-$\beta$-D-glucopyranosyl) C-076 $B_{1a}$

A 3-necked flask is charged with C-076 $B_{1a}$ (50 mg.), 3,4,6-tri-O-acetyl-1,2-O-(ethylorthoacetyl)-$\alpha$-D-glucopyranose (35 mg.), mercuric bromide (2 mg.) and dichloroethane (20 ml.). The reaction mixture is refluxed following the procedure of Example 1. After 12 hours of refluxing, a product forms which is isolated by cooling the reaction mixture, filtering and discarding all solids and evaporating the filtrate in vacuo. Chromatographic resolution of the mixture on preparative layer chromatography [silica gel, multiple development with 19:1 (benzene 12-propanol)] affords a large amount of starting material, small amounts of presumably isomeric glycosides and 3 mg. of 4''-O-(2,3,4,6-tetra-O-acetyl-$\beta$-D-glucopyranosyl C-076 $B_{1a}$. The structure proposed is consistent with mass spectral and 300 MHz nuclear magnetic resonance analysis.

EXAMPLE 3

23-O-(2,2',3,3',4',6,6'-hepta-O-acetyl-$\beta$-maltosyl)C-076 $A_{2a}$

To C-076 $A_{2a}$ (20 mg.) in anhydrous ether (50 ml.) is added freshly prepared silver oxide (60 mg.) and 2,2',3,3',4',6,6'-hepta-O-acetyl-a-acetyl-$\alpha$-maltosyl bromide (51 mg.). The sealed flask is stirred magnetically in the dark. After 24 hours, another 20 mg. of 2,2',3,3',4',6,6'-hepta-O-acetyl-$\beta$-maltosyl bromide is added. After a total of five days, the reaction progress is judged to have stopped, the solids are filtered, washed with ether and discarded. The filtrate is evaporated under a stream of nitrogen and fractionated using preparative layer chromatography on silica gel using multiple development with 2-propanol/benzene (1:19). In addition, to some starting material and other by-products there is obtained 21 mg. of 23-O-(2,2',3,3',4',6,6'-hepta-O-acetyl-$\beta$-maltosyl C-076 $A_{2a}$ (lyophilized from benzene) which is judged to be homogeneous by nuclear magnetic resonance and thin layer chromatography. Mass spectral and 300 MHz nuclear magnetic resonance data are consistent with the product structure.

EXAMPLE 4

13-O-(4-O-acetyl-$\alpha$-L-erythro-2-hexenopyranosyl) C-076 $A_{2a}$ Aglycon

C-076 $A_{2a}$ aglycon (50 mg.) and 3,4-di-O-acetyl-L-rhamnal (50 mg.) are dissolved in benzene (20 ml.), a trace of p-toluenesulfonic acid is added and the mixture is stirred at 80° C. After 4 days the reaction is complete (no more starting material is present by thin layer chromatography). The solvent is evaporated in vacuo and chromatographic resolution of the products [preparative layer chromatography, silica gel using benzene 2-propanol (19:1) multiple development affords one major band which is subsequently resolved into 2 components (using the same separation procedure). By mass spectral and 300 MHz nuclear magnetic resonance analysis the two products are identified as 13-O-(4-O-acetyl-$\alpha$-L-erythro-2-hexenopyranosyl) C-076 $A_{2a}$ aglycon (19 mg.) and 13,23-bis-(4-O-acetyl-$\alpha$-L-erythro-2-hexenopyranosyl) C-076 $A_{2a}$ aglycon (11 mg.).

EXAMPLE 5

23-O-acetyl-4''-O-(2,3,4,6-tetra-O-acetyl-$\beta$-D-glucopyranosyl) C-076 $A_{2a}$ To 23-O-acetyl-C-076 $A_{2a}$ (20 mg.) in anhydrous ether (20 ml.) is added 2,3,4,6-tetra-O-acetyl-$\alpha$-D-glucopyranosyl bromide (70 mg.) and freshly prepared silver oxide (200 mg.). The sealed flask is stirred magnetically in the dark. After four days thin layer chromatography monitoring fails to show any further change in the reaction mixture composition and the solids are filtered, washed with ether and discarded. The filtrate is evaporated under a stream of nitrogen and fractionated with preparative layer chromatography (silica gel) with multiple development using 19:1 (benzene/2-propanol). 23-O-acetyl-4''O-(2,3,4,6-tetra-O-acetyl-$\beta$-D-glucopyranosyl) C-076 $A_{2a}$ (6 mg.) is isolated after lyophilization from benzene in addition to other minor products and a considerable amount of starting material. Mass spectral and 300 MHz nuclear magnetic resonance analysis of the product are consistent with the structure.

EXAMPLE 6

5-O-acetyl-4''-O-(2,3,4,6-tetra-O-acetyl-$\beta$-D-glucopyranosyl) C-076 $B_{1a}$ To C-076 $B_{1a}$ (20 mg.) in anhydrous ether (8 ml.) is added freshly prepared silver oxide (23 mg.) and acetyl chloride (9.5 mg.). The reaction vessel is stirred magnetically under nitrogen in the dark until monoacetylation (at the 5-position) is complete (3–4 hours). Solid powdered sodium bicarbonate is added and the mixture is stirred for an additional hour. The solids are centrifuged and the supernatent containing 5-O-acetyl C-076 $B_{1a}$ with traces of C-076 $B_{1a}$ and 5,4''-di-O-acetyl C-076 $B_{1a}$ (by thin layer chromatography) is poured onto 2,3,4,6-tetra-O-acetyl-$\alpha$-D-glucopyranosyl bromide (25 mg.) and freshly prepared silver oxide (25 mg.). After several days no further reaction progress is noted by thin layer chromatography [two subsequent additions of halogenose and silver oxide (25 mg. each) are made] after 24 and 48 hours of reaction. The solids are filtered, washed with ether and discarded. The filtrate evaporated under a stream of nitrogen and resolved into macrolide components and sugar decomposition products on a short overloaded silica gel column eluting with dichloromethane/methanol (19:1). The macrolide components are resolved on silica gel preparative layer chromatography using multiple development with benzene/isopropanol (95:5). The product is isolated by lyophilization from benzene. Mass spectral and 300 MHz nuclear magnetic resonance data are consistent with the structure of 5-O-acetyl-4''-O-(2,3,4,6-tetra-O-acetyl-$\beta$-D-glucopyranosyl) C-076 $B_{1a}$.

EXAMPLE 7

13-O-(2,3,4,6-tetra-O-acetyl-D-glucopyranosyl) $A_{2a}$ aglycone

A 3-necked flask is charged with C-076 $A_{2a}$ aglycone (30 mg.), 3,4,6-tri-O-acetyl-1,2-O-(ethylorthoacetyl)-$\alpha$-D-glucopyranose (50 mg.), dichloroethane (50 ml.) and mercuric bromide (1 mg.). The flask is fitted with a dropping funnel containing fresh solvent and a Dean-Stark Trap. The mixture is heated at reflux under nitrogen as in Example 1. After 40 hours of refluxing, monitoring by thin layer chromatography indicates no further reaction progress and the mixture is evaporated in vacuo. Resolution on preparative layer chromatography [silica gel, multiple development with benzene (2-propanol (19:1)] affords a large amount of starting merial (31 mg.) and a slower moving band (6 mg.) which is shown by mass spectrometry and 300 MHz nuclear magnetic resonance to be 13-O-(2,3,4,6-tetra-O-acetyl-D-glucopyranosyl) $A_{2a}$ aglycone.

EXAMPLE 8

5-O-(2,3,4,6-tetra-O-acetyl-D-galactopyranosyl)-C-076 $B_{1a}$

C-076 $B_{1a}$ (250 mg.), freshly prepared silver oxide (750 mg.) and 2,3,4,6-tetra-O-acetyl-$\alpha$-D-galactopyransyl bromide (150 mg.) are added to dry ether (100 ml.) in a magnetically-stirred round bottom flask and stirred under nitrogen in the dark for four days. Every 24 hours another 150 mg. of silver oxide and 100 mg. of 2,3,4,6-tetra-O-acetyl-D-galactopyranosyl-C-076 $B_{1a}$ are added (total: 1150 mg. of silver oxide and 350 mg. of 2,3,4,6-tetra-O-acetyl-D-galactopyranosyl C-076 $B_{1a}$. The solids are then filtered and washed with ether. The filtrate is evaporated in vacuo and the residual gum is chromatographed on silica gel (200 gm.) using dichloromethane/methanol (99:1) as eluant. Starting material (C-076 $B_{1a}$, 170 mg.) is recovered as well as an additional product-containing band which is further purified by preparative layer chromatography [multiple development with benzene/2-propanol (19:1)] to furnish the desired product. The product is lyophilized from benzene; spectral analysis is consistent with 5-O-(2,3,4,6-tetra-O-acetyl-D-galactopyranosyl)-C-076 $B_{1a}$.

EXAMPLE 9

4'-O-(3,4-di-O-acetyl-2,6-di-deoxy-L-arabinohexopyranosyl)-C-076 $A_{2a}$ Monosaccharide A 110 ml. round-bottomed flask is charged with C-076 $A_{2a}$ monosaccharide (40 mg.), 3,4-di-O-acetyl-2,6-dideoxy-$\alpha$-L-arabino-hexopyranosyl chloride (diacetyl-olivosyl chloride, 91 mg.), mercuric bromide (216 mg.), mercuric cyanide (250 mg., and dry ether (50 ml). The stoppered flask is stirred in the dark under nitrogen until the reaction appears to make no further progress (by thin layer chromatography; 6 days). Additional quantities of the 3,4-di-O-acetyl-2,6-di-deoxy-L-arabino-hexopyranosyl)chloride (2×63 mg.) are added after 24 and 48 hours. There are seven product bands in addition to a small amount of recovered starting material. Four of the product bands are fluorescent glycosides which have high Rf's in benzene/2-propanol (19:1). The major product is purified to homogeneity by two separate preparative layer chromatography procedures employing multiple developments in the above-named solvent system. The product (24 mg.) is a fluffy white solid after lyophilization from benzene. Mass spectral and 300 MHz nuclear magnetic resonance data are consistent with the structure of 4'-O-(3,4-di-O-acetyl-2,6-dideoxy-L-arabino-hexopyranosyl)-C-076 $A_{2a}$ monosaccharide.

EXAMPLE 10

4'-O-(2,4-di-O-acetyl-2,6-dideoxy-L-arabinohexopyranosyl C-076 $B_{1a}$ monosaccharide-5-one A 100 ml. round-bottomed flask is charged with C-076 $B_{1a}$ monosaccharide-5-one (30 mg.), 3,4-di-O-acetyl-2,6-dideoxy-L-arabino-hexopyranosyl chloride (diacetyl-olivosyl chloride, 30 mg.), freshly prepared silver oxide (400 mg.) and dry ether (25 ml.). The stoppered reaction vessel is stirred in the dark under nitrogen at ambient temperature for 7 days when, by thin layer chromatography [benzene/2-propanol (19:1)], the reaction appears to make no further progress. Four additional 25 mg. quantities of 3,4-di-O-acetyl-2,6-dideoxy-L-arabino-hexopyranosyl chloride are added at 24 hour intervals. During the reaction, the solids are filtered, washed with ether, and discarded. The filtrate is evaporated in vacuo and the colorless gum is resolved by preparative layer chromatography (above system, multiple development) into two major bands: starting material and a slightly faster band, which is chromatographically homogeneous and by spectral analysis consistent with the 4'-O-(2,4-di-O-acetyl-2,6-dideoxy-L-arabino-hexopyranosyl C-076 $B_{1a}$ monosaccharide-5-one.

EXAMPLE 11

4″-O-benzoyl C-076 B$_{1a}$ (from C-076 B$_{1a}$ monosaccharide)

C-076 B$_{1a}$ monosaccharide (35 mg.) is dissolved in dry ether and active manganese dioxide (100 mg.) is added. The mixture is stirred magnetically for 18 hours at room temperature. The reaction mixture is filtered and the solids are washed with ether. The filtrate contains only one spot by thin layer chromatography [tetrahydrofuran/chloroform (9:1)] and the solvent is evaporated in vacuo to afford B$_{1a}$ monosaccharide-5-one as a colorless glass. Ether (25 ml.), 1,5-anhydro-4-O-benzoyl-2,6-dideoxy-3-O-methyl-L-arabino-hex-1-enitol (10 mg.) and pyridinium p-toluenesulfonate (1 mg.) are added and the stoppered vessel is stirred at ambient temperature for an additional 24 hour period. The volatiles are removed in vacuo and methanol (10 ml.) and sodium borohydride (20 mg.) are added to the residual gum. A yellow color developed rapidly which faded within 15 minutes. After stirring for 2 hours under nitrogen, 3 ml. of acetone are added and stirring is continued for an additional hour. The solvents are evaporated in vacuo and the residue resolved on preparative layer chromatography [benzene/2-propanol (19:1)] to furnish the desired compound as the major product. Mass spectral and 300 Mhz nuclear magnetic resonance data are consistent with the structure of 4″-O-benzoyl C-076 B$_{1a}$.

EXAMPLE 12

4′-O-D-glucopyranosyl C-076 A$_{2a}$ monosaccharide (Deprotection using methanolic ammonia)

4′-O-(2,3,4,6-tetra-O-acetyl-D-glucopyranosyl) C-076 A$_{2a}$ monosaccharide (10 mg.) is covered with 10 ml. of methanol which had previously been saturated with anhydrous ammonia at 0° C. The flask is stoppered tightly and stored at ambient temperature for three days. Thin layer chromatography monitoring [trichloromethane/methanol (9:1)] shows no remaining peracetylated materials. The solvent is evaporated under a stream of nitrogen and the product is purified from minor contaminants by preparative layer chromatography on silica gel with the above solvent system as the eluent. The homogeneous product is then lyophilized from benzene affording pure 4′-O-(β-D-glucopyranosyl)C-076 A$_{2a}$ monosaccharide.

EXAMPLE 13

5-O-glucopyranosyl C-076 B$_{1a}$ (Deprotection using catalytic methoxide)

5-O-(2,3,4,6-tetra-O-acetyl-D-glucopyranosyl) C-076 B$_{1a}$ (5 mg.) is dissolved in anhydrous methanol (10 ml.) in a small flask that has been flamed and cooled under nitrogen. A small amount of sodium methoxide powder (3–5 mg.) is added and the stoppered flask is stored at ambient temperature overnight. A chunk of dry ice is added to the reaction mixture before it was evaporated under a stream of nitrogen. The product is separated from minor impurities by preparative layer chromatography on silica gel using dichloromethane/methanol (9:1) as the eluent. 5-O-glucopyranosyl C-076 B$_{1a}$ is obtained in excellent yield as a lyophilized foam (from benzene).

EXAMPLE 14

Following the Koenigs-Knorr Method of Examples 3 or 8 using the appropriate starting materials, the following compounds are prepared:

5-O-peracetyl-L-olivosyl C-076 $B_{1a}$
5-O-peracetyl-L-olivosyl C-076 $B_{1a}$ monosaccharide
5-O-peracetyl-L-rhamnopyranosyl C-076 $B_{1a}$
23-O-peracetyl-L-rhamnopyranosyl C-076 $B_{2a}$
5-O-peracetyl-L-rhamnopyranosyl C-076 $B_{2a}$
5-O-peracetyl-L-arabinopyranosyl C-076 $B_{1a}$ monosaccharide
23-O-peracetyl-L-arabinopyranosyl C-076 $B_{2a}$ monosaccharide
5-O-peracetyl-L-arabinopyranosyl C-076 $B_{2a}$ monosaccharide
5-O-peracetyl-L-lyxopyranosyl C-076 $B_{1a}$
23-O-peracetyl-L-lyxopyranoxyl C-076 $A_{2a}$ monosaccharide
23-O-peracetyl-L-olivosyl C-076 $A_{2a}$
5-O-peracetyl-D-glucopyranosyl-22,23-dihydro C-076 $B_{1a}$
5-O-peracetyl-D-galactopyranosyl-22,23-dihydro C-076 $B_{1a}$
23-O-peracetyl-D-arabinopyranosyl C-076 $A_{2a}$
23-O-peracetyl-D-glucosaminyl C-076 $A_{2a}$
23-O-peracetyl-D-glucuronyl C-076 $A_{2a}$
5-O-peracetyl-D-glucuronyl C-076 $B_{1a}$
23-O-peracetyl-D-mannopyranosyl C-076 $A_{2a}$

EXAMPLE 15

Following the Koenigs-Knorr Method of Example 10, using the appropriate protected starting materials, and reducing the product therefrom by the borohydride reduction method of Example 11, the following products are prepared:

13-O-peracetyl-L-olivosyl C-076 $B_{1a}$ aglycone
13-O-peracetyl-D-maltosyl C-076 $A_{1a}$ aglycone
13-O-peracetyl-D-glucosaminyl C-076 $B_{1a}$ aglycone
13-O-peracetyl-D-glucuronyl-22,23-dihydro C-076 $B_{1a}$ aglycone
4'-O-peracetyl-L-lyxopyranosyl-22,23-dihydro C-076 $B_{1a}$ monosaccharide

EXAMPLE 16

Following the orthoester method of Examples 1,2 or 7, using the appropriate starting materials, the following products are obtained.

4"-O-peracetyl-L-rhamnopyranosyl C-076 $A_{2a}$
4"-O-peracetyl-L-rhamnopyranosyl C-076 $A_{1a}$
4"-O-peracetyl-D-galactopyranosyl C-076 $A_{2a}$
4"-O-peracetyl-D-glucopyranosyl-22,23-dihydro C-076 $B_{1a}$
4'-O-peracetyl-L-lyxopyranosyl C-076 $B_{1a}$ monosaccharide
4'-O-peracetyl-L-rhamnopyranosyl C-076 $B_{1a}$ monosaccharide
4'-O-peracetyl-L-rhamnopyranosyl-22,23-dihydro C-076 $B_{1a}$ monosaccharide

EXAMPLE 17

Following the Helferich modification of Example 9, using the appropriate starting materials, the following products are obtained:

4'-O-peracetyl-L-rhamnopyranosyl C-076 A$_{2a}$ monosaccharide
4'-O-peracetyl-L-olivosyl C-076 A$_{2a}$ monosaccharide
13-O-peracetyl-L-lyxopyranosyl C-076 A$_{2a}$ aglycone
23-O-peracetyl-L-lyxopyranosyl C-076 A$_{2a}$ aglycone
13-O-peracetyl-L-olivosyl C-076 A$_{2a}$ aglycone
23-O-peracetyl-L-olivosyl C-076 A$_{2a}$ aglycone
13-O-peracetyl-L-arabinopyranosyl C-076 A$_{2a}$ aglycone
4'-O-peracetyl-L-oleandrosyl-22,23-dihydro C-076 A$_{1a}$ monosaccharide

EXAMPLE 18

Following the glycal method of Example 4, using the appropriate protecte starting materials, and reducing the product therefrom by the borohydride method of Example 11, the following products are obtained:

4'-O(peracetyl-2-deoxy-D-arabino-hexopyranosyl) C-076 B$_{1a}$ monosaccharide and 4'-O-(peracetyl-2,3-dideoxy-D-enythro-hex-2-enopyranosyl) C-076 $B_{1a}$ monosaccharide-from D-glucal 4'-O-(peracetyl-2-deoxy-L-threo-pentopyranosyl) C-076 $B_{1a}$ monosaccharide and 4'-O-(peracetyl-23-dideoxy-L-glycero-pent-2-enopyranosyl) C-076 $B_{1a}$ monosaccharide-from L-arabinal 4'-O-(peracetyl-2-deoxy-L-erythro-pentopyranosyl) C-076 $B_{1a}$ monosaccharide and 4'-O-(peracetyl-23-dideoxy-L-glycero-pent-2-enopyranosyl) C-076 $B_{1a}$ monosaccharide-from L-xylal 13-O-(peracetyl-2-deoxy-D-lyxo-hexopyranosyl) C-076 $B_1$ aglycone and 13-O-(peracetyl-2,3-dideoxy-D-threo-hex-2-enopyranosyl) C-076 $B_{1a}$ aglycone-from D-galactal 4"-O-isovaleryl-22,23-dihydro C-076 $B_{1a}$ and 4"-O-isovaleryl-3"-deoxy-2,"3"-didehydro C-076 $B_{1a}$ from 4-O-valeryl-L-oleandral

EXAMPLE 19

CHROMATOGRAPHIC MOBILITIES OF PROTECTED C-076 MACROLIDE GLYCOSIDES RELATED TO $A_{2a}$ ON 5 × 20 CM. SILICA GEL THIN LAYER CHROMATOGRAPHY PLATES (DOUBLE DEVELOPMENT)

| COMPOUND NAME | BENZENE/2-PROPANOL(19:1) |
|---|---|
| C-076 $A_{2a}$ (reference) | 0.23 |
| 23-O-(2,3,4,6-tetra-O-acetyl-D-glucopyranosyl)C-076 $A_{2a}$ | 0.24 |
| 23-O-(2,2'3,3',4',6,6'-hepta-O-acetyl-maltosyl) C-076 $A_{2a}$ | 0.30 |
| 4"-O-(2,3,4,6-tetra-O-acetyl-D-glucopyranosyl) C-076 $A_{2a}$ | 0.41 |
| 23-O-acetyl-4"-O-(2,3,4,6-tetra-O-acetyl-D-glucopyranosyl) C-076 $A_{2a}$ | 0.40 |
| $A_{2a}$ monosaccharide (reference) | 0.34 |
| 4'-O-(2,3,4,6-tetra-O-acetyl-D-glucopyranosyl) C-076 $A_{2a}$ monosaccharide | 0.45 |
| 23-O-(2,3,4,6-tetra-O-acetyl-D-glucopyranosyl) C-076 $A_{2a}$ monosaccharide | 0.33 |
| 4'-O-(3,4-di-O-acetyl-2,6-dideoxy-L-arabino-hexopyranosyl) C-076 $A_{2a}$-monosaccharide (olivosyl) | 0.44 |
| C-076 $A_{2a}$ aglycone (reference) | 0.38 |
| 23-O-(2,3,4,6-tetra-O-acetyl-D-glucopyranosyl) C-076 $A_{2a}$ aglycone | 0.37 |
| 13-O-(2,3,4,6-tetra-O-acetyl-D-glucopyranosyl) C-076 $A_{2a}$ aglycone | 0.26 |
| 13-O-(4-D-acetyl-2,3,6-trideoxy-α-L-erythro-Hex-2-enopyranosyl) c-076 $A_{2a}$ aglycone | 0.48 |
| 13,23-Bis-O-(4-O-acetyl-2,3,6-trideoxy-α-L-erythro-hex-2-enopyranosyl) C-076 $A_{2a}$ aglycone | 0.55 |

EXAMPLE 20

CHROMATOGRAPHIC MOBILITIES OF DEPROTECTED C-076 MACROLIDE GLYCOSIDES 5 × 20 CM. SILICA GEL THIN LAYER CHROMATOGRAPHY PLATES (SINGLE DEVELOPMENT)

| COMPOUND NAME | DICHLOROMETHANE/METHANOL(9:1) |
|---|---|
| C-076 $A_2$ (reference) | 0.58 |
| 4"-O-D-glucopyranosyl C-076 $A_2$ | 0.55 |
| 4'-O-D-glucopyranosyl C-076 $A_{2a}$ monosaccharide | 0.57 |
| C-076 $B_2$ (reference) | 0.46 |
| 23-O-maltosyl C-076 $B_{2a}$ | 0.42 |
| 23-O-D-glucopyranosyl C-076 $B_{2a}$ monosaccharide | 0.47 |

EXAMPLE 21

CHROMATOGRAPHIC MOBILITIES OF PROTECTED C-076 MACROLIDE GLYCOSIDES RELATED TO $B_{1a}$ OR $B_{2a}$ 5 × 20 SILICA GEL THIN LAYER CHROMATOGRAPHY PLATES (DOUBLE DEVELOPMENT)

| COMPOUND NAME | BENZENE/2-PROPANOL(19:1) |
|---|---|
| C-076 $B_{1a}$ (reference) | 0.18 |
| 5-O-acetyl-4"-O-(2,3,4,6-tetra-O-acetyl-D-glucopyranosyl) C-076 $B_{1a}$ | 0.33 |
| 5-O-acetyl-4"-O-(2,3,4,6-tetra-O-acetyl-D-acetyl-D-glucopyranosyl C-076 $B_{1a}$ | 0.32 |

EXAMPLE 21
CHROMATOGRAPHIC MOBILITIES OF PROTECTED C-076 MACROLIDE GLYCOSIDES RELATED TO $B_{1a}$ OR $B_{2a}$ 5 × 20 SILICA GEL THIN LAYER CHROMATOGRAPHY PLATES (DOUBLE DEVELOPMENT)

| COMPOUND NAME | BENZENE/2-PROPANOL(19:1) |
|---|---|
| 5-O-(2,3,4,6-tetra-O-acetyl-D-galactopyranosyl) C-076 $B_{1a}$ | 0.26 |
| 4'-O-(3,4-di-O-acetyl-2,6-dideoxy-L-arabino hexopyranosyl)-C-076 $B_{1a}$ monosaccharide-5-one (olivosyl) | 0.41 |
| 5-O-(2,3,4,6-tetra-O-acetyl-D-glucopyranosyl) C-076 $B_{1a}$ monosaccharide | 0.21 |
| C-076 $B_{2a}$ (reference) | 0.15 |
| 23-O-(2,2',3,3',4',6,6'-hepta-O-acetyl-maltosyl) C-076 $B_{2a}$ | 0.18 |
| 23-O-(2,3,4,6-tetra-O-acetyl-D-glucopyranosyl) C-076 $B_{2a}$ | 0.20 |

PREPARATION 1

Glycal synthesis 4-O=benzoyl-L-oleandral

A mixture of 40% sodium hydroxide (75 ml.) diethyl ether (200 ml.) are stirred in an ice bath, while 16.0 g. of nitrosomethylurea is added in portions over a period of 20 min. The mixture is stirred for an additional hour in the ice bath and the ether solution then decanted and dried over sodium hydroxide pellets.

To a solution of L-rhamnal (*Methods in Carbohydrate Chemistry*, Vol. II, p. 407–8), 2.1 g. in diethyl ether (200 ml.), is added stannous chloride dihydrate (200 mg.) in 20 ml. of ether followed by about one third of the diazomethane solution. The reaction mixture remains at room temperature (23° C.) and after 30 min. another 200 mg. of the diazomethane solution. The reaction is stirred overnight (18 hrs.) and silica gel t/c (dichloromethane/methanol, 19:1) shows the reaction to be essentially complete. Acetic acid is added to dispose the yellow color and the mixture is filtered through Supercel. The filtrate is washed with 10% sodium bicarbonate solution and then with saturated salt solution. The solution is dried and evaporated to a residue, which is then purified to the homogeneity by silica gel chromatography (dichloromethane/rhamnal) as a colorless syrup (77%).

The methylation product (2.23 g) is dissolved in pyridine (20 ml.) and stirred with cooling while 2.25 ml. of benzoyl chloride is added. The temperature rises slightly and a light precipitate forms. The cooling bath is removed after two hours and stirring maintained for 48 hrs. Water is then added (15 drops) and after 45 min., 200 ml. of dichloromethane. The mixture is washed with 1 N HCl until the extracts are acidic and then with sodium bicarbonate solution and finally saturated salt solution. The organic phase is dried and the solvent removed in vacuo to furnish a colorless syrup, which could be purified further by silica gel chromatography using (99:1) dichloromethane/tetrahydrofuran as the eluant to furnish 3.6 g of protected glycal.

The product contains a small amount of the 4-O-methyl isomer, which could be resolved by silica gel high performance liquid chromatography using 7.5% ethyl acetate in n-hexane as eluant.

PREPARATION 2

Of glycosylhalide synthesis

L-olivosyl chloride

(2,6-dideoxy-3,4-di-O-acetyl-L-arabinohexopyranosyl chloride

Dry hydrogen chloride gas is bubbled slowly into a benzene solution of 3,4-di-O-acetyl-L-rhamnal (7.5 g. in 50 ml. benzene). The solution is cooled in an ice salt bath. When the solution is saturated (about 20 min.), the addition of hydrogen chloride is discontinued and the mixture allowed to stand at 0° C. for one hour. The solvent is then removed under vacuum and toluene (50 ml.) added and removed in vacuo (high vacuum) three times. The residual oil is dissolved in ether at 0° C. and petroleum ether (30°–60° C.) added to induce crystallization. The colorless crystals are filtered under nitrogen washed with petroleum ether and dried on the funnel under a stream of nitrogen before storage at −5° C. (6.8 g.).

PREPARATION 3

C-076 A1a Aglycone

100 Mg. of C-076 A1a is dissolved in 5 ml. of dioxane, stirred and added at room temperature to a mixture of 0.1 ml. of concentrated sulfuric acid, 1.9 ml. of methanol and 3.0 ml. of dioxane. The reaction mixture is stirred overnight at room temperature. 473 Mg. of solid sodium bicarbonate is added and the mixture stirred for 20 minutes. 3 Ml. of water is added and stirred for an additional 10 minutes. The reaction mixture is concentrated and 40 ml. of chloroform is added and shaken. The aqueous layer is separated and extracted with 5 ml. of chloroform. The organic layers are combined and washed once with dilute sodium chloride solution, dried over magnesium sulfate and evaporated to dryness in vacuo. ¼ of the residue is placed on 5 preparative layer chromatography silica gel plates and eluted with 2% methanol in chloroform affording 4 bands of material. The remainder of the material is run on 2 preparative layer chromatography plates eluting with 2% methanol in chloroform affording 4 band similar to the first series. The second fastest bands are removed from each of the plates combined, extracted and evaporated to dryness in vacuo, and rechromatographed on a preparative layer chromatography silica gel plate eluting with 3% tetrahydrofuran and chloroform affording 9.4 mg. of a fluffy white solid which is identified by mass spectrometry as C-076 A1a aglycone.

PREPARATION 4

C-076 A2a Aglycone

2 G. of C-076 A2a is combined with 40 ml. of a 1% (volume/volume) solution of concentrated sulfuric acid in methanol. The reaction mixture is stirred at room temperature for 17 hours and diluted with 300 ml. of chloroform. The mixture is washed once with 30 ml. of saturated sodium bicarbonate solution, once with 30 ml. saturated sodium chloride solution, dried over magnesium sulfate and evaporated to dryness in vacuo. 5 Ml.

of methanol is added to the residue and allowed to stand at room temperature overnight. Cooling of the mixture in ice causes the slow precipitation of crystals. A supernatant is removed and the solid crystals washed twice with 1 ml. of cold methanol affording 340 mg. of a white solid. The mother liquor and washings are evaporated down to a volume of about 2 ml. and allowed to stand affording an additional crop to crystals. 630 Mg. of a white solid is obtained which is combined with the first batch of crystals and 8 ml. of methanol and evaporated to a volume of 2.5 ml. and allowed to stand for several hours. 910 Mg. of an off white solid is obtained which mass spectrometry identifies as C-076 A2a aglycone.

PREPARATION 5

C-076 A2a Monosaccharide

500 Mg. of C-076 A2a is dissolved in 10 ml. of a solution of 0.1 ml. of concentrated sulfuric acid and 9.9 ml. of isopropanol. The reaction mixture is stirred at room temperature overnight. 125 Ml. of chloroform is added and the mixture washed once with 10 ml. of saturated sodium bicarbonate and once with 10 ml. of water. The organic layer is dried over magnesium sulfate and evaporated to dryness in vacuo affording a pale yellow solid material which is dissolved in chloroform and placed on 5 preparative layer chromatography silica gel plates and eluted twice with 2% benzene in ethylacetate. The slower moving major fraction contains 367 mg. of a white powder after lyophilization from benzene which mass spectrometry and 300 MHz nuclear magnetic resonance indicates is C-076 A2a monosaccharide.

PREPARATION 6

C-076 B1a Monosaccharide and C-076 B1a Aglycone 2.5 Ml. of a solution consisting of 0.5 ml. of water 0.5 ml. concentrated sulfuric acid and 9.0 ml. of dioxane is added and the reaction mixture stirred at room temperature for 17 hours. 50 Ml. of ether is added followed by 25 ml. of saturated aqueous sodium bicarbonate solution. The two layer mixture is shaken, the aqueous layer separated and the organic layer washed with water, dried and evaporated to dryness in vacuo. Benzene is added to the residue and the benzene layer is dried and lyophilized affording 60 mg. of yellow material. The material is placed on a preparative layer chromatography silica gel plate and eluted with chloroform-tetrahydrofuran in the volume ratio of 9:1 and 2 bands are observed with an Rf of 0.15 and 0.35. 300 MHz nuclear magnetic resonance identifies the two spots as C-076 B1a monosaccharide and C-076 B1a aglycone respectively. 16 Mg. of each fraction is obtained.

PREPARATION 7

C-076 B1a Monosaccharide

100 Mg. of C-076 B1a is dissolved in 5.0 ml. of tetrahydrofuran and stirred at room temperature while 5.0 ml. of a cold aqueous solution of 10% sulfuric acid (volume/volume) is added dropwise with stirring. The reaction mixture is stirred at room temperature for 18 hours. 75 Ml. of methylene chloride and 25 ml. of saturated aqueous sodium bicarbonate is added and the layers shaken and separated. The organic layer is washed with aqueous sodium chloride solution and an equal volume of water. The organic layer is dried and evaporated to dryness in vacuo affording 70 mg. of a colorless oil. High pressure liquid identifies the residual oil as C-076 B1a monosaccharide.

PREPARATION 8

C-076 B2a Aglycone

2 G. of C-076 B2a is combined with 40 ml. of a 1% solution of concentrated sulfuric acid in methanol (volume/volume). The reaction mixture is stirred at room temperature for 17 hours. 300 Ml. of chloroform is added followed by 30 ml. of an aqueous saturated sodium bicarbonate solution. The layers are separated and the organic layer washed with 30 ml. of saturated sodium chloride solution, dried over magnesium sulfate and evaporated to dryness in vacuo. 5 Ml. of methanol is added to dissolve the residue and the mixture allowed to stand at room temperature and then cooled in an ice bath, whereupon crystallization occurs. The supernatant is removed and the residue washed twice with 1 ml. portions of cold methanol and the solid crystals dried overnight and then in vacuo at 35° C. affording 1.0 g. of white crystals. A second crop is obtained by evaporating the mother liquors to a volume of 2 ml. and allowing to stand overnight at room temperature. 2 Ml. of methanol is added and the mixture aged in an ice bath affording 140 mg. of a yellow solid. The two solid fractions are combined and dissolved in boiling methanol, about 30 ml. of methanol is required. The solution is filtered hot and concentrated to a volume of about 20 ml. in vacuo whereupon solids begin to precipitate. The solution is filtered hot and the solid materials washed with methanol affording 340 mg. of a white solid. The filtrates are boiled down to a volume of about 8 ml. and set aside to crystallize at room temperature affording 433 mg. of a white solid. Mass spectrometry shows the two fractions to be identical and to be identified as C-076 B2a aglycone.

PREPARATION 9

C-076 B2a Monosaccharide and C-076 B2a Aglycone

20 Mg. of C-076 B2a is combined with 4 ml. of a solution prepared by combining 0.1 ml. of concentrated sulfuric acid and 9.9 ml. of isopropanol. The reaction mixture is stirred at room temperature for 16 hours, 189 mg. of sodium bicarbonate is added followed by a few drops of water. The volume is reduced to about ½ and 30 ml. of chloroform and 3 ml. of water is added and the mixture shaken. The layers are separated and the aqueous layer extracted with an additional 5 ml. of chloroform. The organic layers are combined, washed once with dilute sodium chloride solution, dried over sodium sulfate and magnesium sulfate and evaporated to dryness in vacuo. The residue is placed on two preparative layer silica gel chromatography plates and eluted twice with 5% tetrahydrofuran in chloroform. 4 Bands of material are observed and individually removed from the preparative chromatography plates. The slowest band affords 7.3 mg. of a white solid which is identified by mass spectrometry as C-076 B2a monosaccharide. The next slowest band affords 1.3 mg. of a white solid and it is identified by mass spectrometry as C-076 B2a aglycone.

PREPARATION 10

22,23-Dihydro C-076 A1a 51.0 Mg. of C-076 A1a and 14.4 mg. of tris (triphenylphosphine)rhodium (I) chloride are combined in 3.5 ml.

of benzene and hydrogenated for 20 hours at room temperature under atmospheric pressure. The crude reaction mixture is chromatographed on a preparative layer chromatography plate eluting twice with 10% tetrahydrofuran in chloroform. The product is removed from the support using ethyl acetate which is evaporated to dryness and the residue analyzed with 300 MHz nuclear magnetic resonance and mass spectroscopy indicating the preparation of 22,23-dihydro C-076 A1a.

PREPARATION 11

22,23-Dihydro C-076 B1a

A solution of 1.007 g. of C-076 B1a, 314 mg. of tris(-triphenylphosphine)rhodium(I)chloride and 33 ml. of benzene is hydrogenated for 21 hours at room temperature under 1 atmosphere of hydrogen pressure. The solvent is removed in vacuo and the residue dissolved in a 1:1 mixture of methylene chloride and ethyl acetate and filtered. The filtrate is placed on a column of 60 g. of silica gel eluting with a 1:1 mixture of methylene chloride and ethyl acetate taking 10 ml. fractions. Fractions 14–65 are combined and evaporated to dryness affording 1.118 g. of a solid material which is indicated by high pressure liquid chromatography to be a 60/40 mixture of the hydrogenated product and starting material. The mixture is rehydrogenated in 55 ml. of benzene adding 310 mg. of tris (triphenylphosphine) rhodium (I) chloride and stirring for 21 hours at room temperature under 1 atmosphere of hydrogen pressure. The solvent is removed in vacuo and the residue chromatographed on 80 g. of silica gel using 40:60 mixture of ethyl acetate and methylene chloride as eluant. 10 Ml. fractions are taken and the product appears in fractions 26–80. These fractions are combined and evaporated to dryness in vacuo affording a yellow oil. The oil is dissolved in benzene and lyophilized affording a pale yellow powder which is identified as 22,23-dihydro C-076 B1a by mass spectrometry and 300 MHz nuclear magnetic resonance. 0.976 G. of product is obtained.

PREPARATION 12

22,23-Dihydro C-076 B1a Monosaccharide

395 Mg. of 22,23-dihydro C-076 B1a is added to a stirred solution of 50 ml. of 1% sulfuric acid in isopropanol and the solution is stirred for 14 hours at room temperature. The reaction mixture is treated as in Example 4 affording 0.404 g. of a foam after lyophilization from benzene. The foam is chromatographed on 6 preparative layer silica gel chromatography plates eluting twice with 4% tetrahydrofuran in chloroform. The monosaccharide with a Rf 0.15 is collected and washed from the silica gel with a total of 650 ml. of ethyl acetate. The combined washings are evaporated to dryness and the residue lyophilized from benzene to afford 0.2038 g. of 22,23-dihydro C-076 B1a monosaccharide which high pressure liquid chromatography indicates to be essentially pure.

PREPARATION 13

22,23-Dihydro C-076 B1a Aglycone 0.486 G. of 22,23-dihydro C-076 B1a is added to a stirred solution of 50 ml. of 1% sulfuric acid in methanol and the reaction mixture stirred for 13 hours at room temperature. The reaction mixture is diluted with 250 ml. of methylene chloride and washed with 50 ml. of saturated aqueous potassium bicarbonate and 50 ml. of water. The aqueous layer is washed twice with 20 ml. portions of methylene chloride and the combined organic phases are dried with saturated brine and sodium sulfate and evaporated to dryness in vacuo affording 0.480 g. of a pale yellow foam. The foam is dissolved in 4 ml. of methylene chloride and placed on 4 preparative layer chromatography silica gel plates and eluted 4 times with 4% tetrahydrofuran and chloroform. The product is recovered from the silica gel plates affording an oily residue which is lyophilized from benzene affording 255.8 mg. of a white solid. Traces of methyl oleandroside are indicated to be present in the solid material. The white solid is then lyophilized again from benzene and placed under high vacuum for 20 hours to remove the impurity affording 22,23-dihydro C-076 B1a aglycone.

PREPARATION 14

A. C-076 A1a 4"-O-Acetate

A solution of 27 mg. of 4-dimethylaminopyridine in 1 ml. of methylene chloride is prepared and a separate solution of 0.208 ml. of acetic anhydride in 10 ml. of methylene chloride is prepared. 0.5 Ml. of each solution is added to 10 mg. of C-076 A1a, mixed well and allowed to stand at room temperature overnight. The reaction mixture is diluted to 4 ml. with methylene chloride and 0.5 ml. of water is added and shaken. The layers are separated and the organic layer is dried over magnesium sulfate and evaporated to dryness under a stream of nitrogen. Benzene is added and the solution is lyophilized affording 10 mg. of an off-white fluffy solid. Preparative layer chromatography on silica gel eluting with 10% tetrahydrofuran in chloroform affords 8.2 mg. of a fluffy, off-white solid, which nuclear magnetic resonance and mass spectrographic analysis reveals to be C-076 A1a 4"-O-acetate.

B. C-076 A2a 4"-O-Acetate

Following the above procedure 5 mg. of C-076 A2a is acetylated affording 4.4 mg. of a product which is demonstrated by mass spectrometry and nuclear magnetic resonance to be C-076 A2a 4"-O-acetate.

C. C-076 A2a 4",23-di-O-acetate

10 Mg. of C-076 A2a is acetylated in 0.5 ml. of pyridine and 0.25 ml. acetic anhydride at 100° C. for 2 hours. The reaction mixture is worked up using preparative layer chromatography on silica gel as previously described affording 5.9 mg. of a fluffy white solid which mass spectrometry and nuclear magnetic resonance reveal to be C-076 A2a 4",23-O-acetate.

PREPARATION 15

C-076 A2a 4" O-Propionate

25 Mg. of C-076 A2a is combined with 15 drops of dry pyridine and cooled in ice while 5 drops of propionic anhydride is added. The reaction mixture is stoppered, mixed well and allowed to stand in an ice bath overnight. The reaction mixture is diluted with ether and benzene and shaken with some ice water. The layers are separated and the organic layer is dried over magnesium sulfate. The solvent is evaporated under a stream of nitrogen, benzene is added and the solution is lyophilized affording 20 mg. of a white solid. Preparative layer chromatography on silica gel eluting with 5% tetrahydrofuran in chloroform affords 16.6 mg. of a white solid which is analysed by nuclear magnetic resonance and mass spectrometry as C-076 A2a 4″-O-propionate.

PREPARATION 16

C-076 B1a 4″,5-di-O-acetate

Following the procedure of Preparation 14, 5.2 mg. of C-076 B1a is acetylated with 10 drops of pyridine and 6 drops of acetic anhydride affording, after preparative layer chromatography on silica gel and lyophilization, 5.2 mg. of a white fluffy solid which mass spectrometry indicates is C-076 B1a 4″,5-di-O-acetate.

PREPARATION 17

C-076 B1a 4″,O-Acetate and C-076 B1a 4″,5-Di-O-Acetate

20 Mg. of C-076 B1a is dissolved in 12 drops of pyridine, cooled in an ice bath and combined with 4 drops of acetic anhydride. The reaction mixture is maintained in an ice bath for 2½ hours, chilled benzene is added, the reaction mixture freeze dried and the solid material chromatographed on silica gel plates eluting with 10% isopropanol in benzene. The product with the highest Rf is identified by mass spectrometry as C-076 B1a 4″, 5-di-O-acetate, 4.7 mg. is obtained. The next most advanced spot is identified by mass spectrometry as C-076 B1a 4″,O-acetate; 9.3 mg. is obtained.

What is claimed is:
1. A compound having the formula:

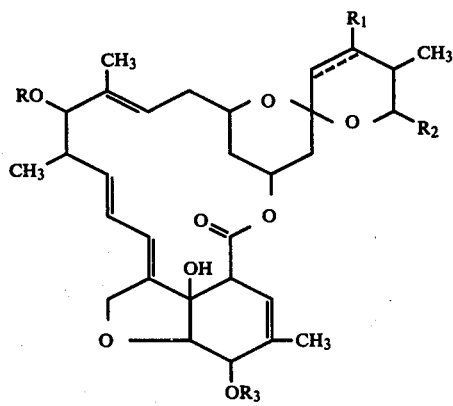

wherein the broken line indicates a single or double bond;
$R_1$ is hydroxy, loweralkanoyloxy, or glycosyloxy and is present only when the broken line indicates a single bond;
$R_2$ is n-propyl or sec-butyl;
$R_3$ is hydrogen, methyl, loweralkanoyl or glycosyl; and
R is hydrogen, loweralkanoyl, glycosyl,

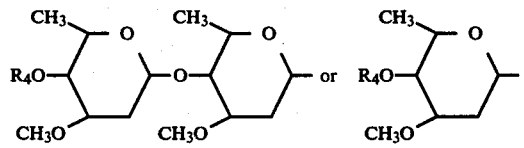

wherein $R_4$ is hydrogen, loweralkanoyl or glycosyl; wherein said glycosyl groups are polyhydroxy 5- or 6-membered cyclic acetals which are optionally substituted on the ring carbon atoms with loweralkyl and in which the hydroxy groups may be optionally substituted with loweralkyl or loweralkanoyl, and the monosaturated glycosyl derivatives thereof;
provided that at least one of R, $R_1$, $R_3$ or $R_4$ must contain a glycosyl group, however, when only R contains a glycosyl group, said glycosyl group of R shall exclude the α-L-oleandrosyl and α-L-oleandrosyl-α-L-oleandrosyl groups.

2. A compound of claim 1 wherein the glycosyl moiety of R, $R_1$, $R_3$, or $R_4$ is a mono, di or trisaccharide with the following groups which may be the same or different in the di and trisaccharides and are glucopyranosyl, galactopyranosyl, mannopyranosyl, maltosyl, arabinopyranosyl, lyxopyranosyl, xylopyranosyl, ribopyranosyl, oleandrosyl, rhamnopyranosyl, fucopyranosyl, lactosyl, ribofuranosyl, mannofuranosyl, glucofuranosyl, arabinofuranosyl, mycarosyl, cladinosyl, desosaminosyl, daunosaminosyl, mycaminosyl, cymarosyl or olivosyl.

3. A compound of claim 2 wherein the glycosyl moiety is a mono- or disaccharide with the following groups which may be the same or different in the disaccharide and are glucopyranosyl, rhamnopyransoyl, oleandrosyl, or daunosaminosyl.

4. A compound of claim 3 wherein the glycosyl moiety is a mono- or disaccharide with the following groups which may be the same or different in the disaccharide and are glucopyranosyl or oleandrosyl.

5. The compound of claim 2 which is 4′-O-(2,3,4,6-tetra-O-acetyl-β-D-glucopyranosyl C-076 A2a monosaccharide.

6. The compound of claim 2 which is 4″-O-(2,3,4,6-tetra-O-D-glucopyranosyl) C-076 B1a.

7. The compound of claim 2 which is 23-O-(2,2′, 3,3′,4′,6,6′-hepta-O-acetyl-β-maltosyl) c-076 A2a.

8. The compound of claim 2 which is 13-O-(4-O-acetyl-α-L-erythro-2-hexenoyranosyl) C-076 A2a Aglycon.

9. The compound of claim 2 which is 23-O-acetyl-4″-O-(2,3,4,6-tetra-O-acetyl-β-D-glucopyranosyl) C-076 A2a.

10. The compound of claim 2 which is 5-O-acetyl-4″-O-(2,3,4,6-tetra-O-acetyl-β-D-glucopyranosyl) C-076 B1a.

11. The compound of claim 2 which is 13-O-(2,3,4,6-tetra-O-acetyl-D-glucopyranosyl) A2a aglycone.

12. The compound of claim 2 which is 5-O-(2,3,4,6-tetra-O-acetyl-D-galactoyranosyl)C-076 B1a.

13. The compound of claim 2 which is 4′-O-(3,4-di-O-acetyl-2,6-di-deoxy-L-arabinohexoyranosyl)-C-076 A2a monosaccharide.

14. The compound of claim 2 which is 4′-O-(2,4-di-O-acetyl-2,6-dideoxy-L-arabinohexopyranosyl C-076 B1a monosaccharide-5-one.

15. The compound of claim 2 which is 4′-O-D-glucopyranosyl C-076 A2a monosaccharide.

16. The compound of claim 2 which is 5-O-glucopyranosyl C-076 B1a.

17. A method for the treatment of helmintic, arthropod ectoparasitic, and acaridal infections which comprises administering to an animal infected with such helminths, arthropod ectoparasites or acarides an effective amount of a compound of claim 1.

18. A composition useful for the treatment of helmintic, arthropod ectoparasitic and acaridal infections which comprises a compound of claim 1 and an inert carrier.

* * * * *

UNITED STATES PATENT AND TRADEMARK OFFICE
CERTIFICATE OF CORRECTION

PATENT NO. : 4,203,976
DATED : May 20, 1980
INVENTOR(S) : Michael H. Fisher et al.

It is certified that error appears in the above—identified patent and that said Letters Patent is hereby corrected as shown below:

On Column 2, line 5 and Column 25, line 53, delete "n-propyl" and insert therefor --isopropyl--

Signed and Sealed this

Seventeenth Day of February, 1987

Attest:

DONALD J. QUIGG

Attesting Officer

Commissioner of Patents and Trademarks